United States Patent [19]

Wepplo et al.

[11] 4,197,311

[45] Apr. 8, 1980

[54] CYANOMETHYL TRITHIOCARBONATE COMPOUNDS USEFUL AS OVICIDAL AGENTS

[75] Inventors: Peter J. Wepplo, Princeton; Donald P. Wright, Jr., Pennington, both of N.J.

[73] Assignee: American Cyanamid Company, Stamford, Conn.

[21] Appl. No.: 942,590

[22] Filed: Sep. 15, 1978

[51] Int. Cl.$^2$ .................. A01N 9/28; C07C 154/02; C07D 307/64; A01N 9/12
[52] U.S. Cl. .................. 424/285; 260/455 R; 260/455 B; 260/347.2; 424/301
[58] Field of Search ............ 260/455 R, 455 B, 347.2; 424/301, 285

[56] References Cited

U.S. PATENT DOCUMENTS 2,731,487  1/1956  Bashour ........................... 260/347.2

OTHER PUBLICATIONS

Whitmore, Organic Chemistry, D. Van Nostrand Company, Inc., New York, (1951), p. 144.
Reid, Organic Chemistry of Bivalent Sulfur, Chemical Publishing Co., Inc., New York (1962), pp. 177-179 (vol. IV).

*Primary Examiner*—Alan L. Rotman
*Assistant Examiner*—Robert C. Whittenbaugh
*Attorney, Agent, or Firm*—H. G. Jackson

[57] ABSTRACT

The invention is novel cyanomethyl trithiocarbonate compounds which are useful ovicidal agents effective for the control of insects and acarina.

20 Claims, No Drawings

CYANOMETHYL TRITHIOCARBONATE COMPOUNDS USEFUL AS OVICIDAL AGENTS

The invention relates to novel cyanomethyl trithiocarbonate compounds represented by the formula:

$$R-S-CS-SCH_2-CN \quad (I)$$

wherein R is a α-methylbenzyl,

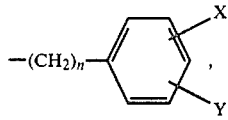

cycloalkyl $C_3$–$C_6$ optionally substituted with methyl, furfuryl or cycloalkyl $C_3$–$C_6$ methyl; X and Y each represent H, Cl, $CH_3$ or $OCH_3$ and n is an integer selected from 1, 2 and 3.

The invention also relates to a method for controlling insects and acarina, particularly plant mites, comprising contacting the ova of the insects and acarina, with an ovicidally effective amount of a cyanomethyl thiocarbonate compound represented by formula II $$R-Z-CS-SCH_2-CN \quad (II)$$

wherein Z is S or O, R is alkyl $C_1$–$C_8$, α-methylbenzyl,

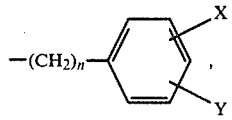

cycloalkyl $C_3$–$C_6$ optionally substituted with methyl, furfuryl or cycloalkyl $C_3$–$C_6$ methyl; X and Y each represent H, Cl, $CH_3$ or $OCH_3$ and n is an integer selected from 1, 2 and 3. The invention further relates to a method for the preparation of the formula I cyanomethyl trithiocarbonate compounds. Insecticides of the formula $RO-CS-S-CH_2-CN$ where R is alkyl are taught in Sumitomo's Japanese Pat. No. 19075/66.

Preferred insect ovicidal compounds of this invention have the structure of formula I wherein R is alkyl $C_1$–$C_8$, α-methylbenzyl, furfuryl, cyclohexyl or

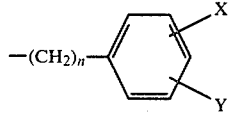

where n is an integer selected from 1, 2 and 3; X is H, Cl, $CH_3$ or $OCH_3$ and Y is H or Cl, provided that when Y is Cl, X is H or Cl; and most preferred of these insect ovicides are compounds, as described, where R is p-chlorobenzyl, benzyl, p-methoxybenzyl, cyclohexyl, alkyl $C_2$–$C_4$, and phenylethyl. These latter compounds have the added advantage of low phytotoxicity to crops even at the highest rates of application employed in ovicidal applications. This reduced phytotoxicity is, of course, important in the treatment of crops since excessive injury to crop plants will ultimately reduce crop yields and/or reduce the market value of the crop produced through discoloration or marking of the fruit produced by the treated plants.

Preferred mite ovicides also have the structure of formula I, however, the preferred compounds are those wherein R is sec-butyl, isobutyl, alkyl $C_5$–$C_8$, α-methylbenzyl, furfuryl, cyclohexyl, methylcyclohexyl or

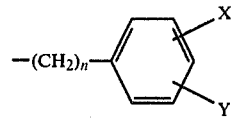

where n is an integer selected from 1, 2 and 3; X is H, Cl, $CH_3$ or $OCH_3$ and Y is H or Cl, provided that when Y is Cl, X is H or Cl.

The trithiocarbonate compounds of this invention can be prepared by reacting a mercaptan having the structure:

RSH where R is alkyl $C_1$–$C_8$, furfuryl,

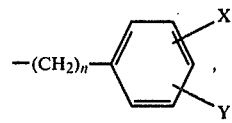

cycloalkyl $C_3$–$C_6$ optionally substituted with methyl or cycloalkyl $C_3$–$C_6$ methyl; X and Y each represent H, Cl, $CH_3$ or $OCH_3$ and n is an integer selected from 1, 2 and 3; with an alkali metal hydride, such as lithium or sodium hydride; or an alkali metal hydroxide, such as lithium, sodium or potassium hydroxide; or an alkali metal alkoxide, such as sodium, lithium or potassium alkoxide of a $C_1$–$C_5$ alcohol in the presence of alcohol, ether, especially tetrahydrofuran, hydrocarbon, and the like, solvents or mixtures thereof followed by carbon disulfide. The reaction is generally carried out at a temperature between about 10° and 30° C. and then adjusted to about 15° to 20° C. before introducing carbon disulfide into the reaction mixture. After stirring to allow complete formation of the trithiocarbonate salt, chloroacetonitrile is added to the reaction mixture at between about 15° and 20° C. After stirring, the reaction mixture is then concentrated, taken up in ether and the thus formed solution washed with water and brine and then dried, as for example, with sodium sulfate. The resulting solution is then concentrated to give the crude product. The crude product may be further purified by several means including crystallization, distillation, chromatography or the like.

Examples of these reactions are graphically illustrated below:

$$RSH + R^2OM + CS_2 \rightarrow RS-CS-SM$$

where R is as described above; $R^2$ is alkyl $C_1$–$C_6$ and M is an alkali metal of sodium, lithium or potassium.

$$RS-CS-SM + ClCH_2CN \xrightarrow{THF} RS-CS-SCH_2CN$$

Alternatively, the cyanomethyl trithiocarbonates of this invention can be prepared by first reacting the appropriate mercaptan with an alkali metal hydride, such as lithium or sodium hydride; or an alkali metal hydroxide, such as lithium, sodium or potassium hydroxide; or an alkali metal alkoxide, such as sodium, lithium or potassium alkoxide of a $C_1$–$C_5$ alcohol in the presence of alcohol, ether, especially tetrahydrofuran, hydrocarbon and the like, solvents or mixtures thereof and then treating the reaction mixture with carbon disulfide to form the trithiocarbonate salt. This salt is isolated either by filtration or by evaporation of the reaction solvent. The salt may then be dissolved in a solvent such as an alcohol, ether, especially tetrahydrofuran, ketone, hydrocarbon or the like and treated with chloroacetonitrile to yield the desired cyanomethyl trithiocarbonate.

A still further method for the preparation of the trithiocarbonates of this invention involves the use of a two-phase reaction medium to which a phase transfer catalyst may be added to assist in the transfer of the trithiocarbonate from the aqueous phase of the reaction mixture to the organic phase from which the cyanomethyl trithiocarbonate is readily recovered.

In the process the appropriate mercaptan is dispersed in water containing an alkali metal hydroxide. An organic solvent such as toluene, benzene or xylene is added and a phase transfer catalyst is introduced. The reaction mixture is then treated with carbon disulfide and thereafter chloroacetonitrile is added. The aqueous phase is then separated from the organic phase and the cyanomethyl trithiocarbonate recovered from the organic phase by the workup procedures utilized in the process techniques described above.

Among the phase transfer catalysts which may be employed in this process are: tri($C_3$-$C_{12}$)alkylamines, tri($C_3$-$C_{12}$)alkylmethylammonium salts, benzyltri($C_2$-$C_3$)-alkylammonium salts, tetrabutyl ammonium bisulfate and the like.

In practice it is preferred to conduct the described reactions using approximately equimolar amounts of the mercaptan, alkali metal hydroxide, carbon disulfide and chloroacetonitrile. It is likewise preferred to maintain the temperature of the reaction mixture between about 10° and 25° C. during the entire process.

Advantageously, the cyanomethyl trithiocarbonates represented by formula I above are highly effective ovicidal agents useful for inhibiting the hatching of eggs of insects and acarina and/or for preventing the development and maturation of the newly hatched larvae or nymphs of the pests.

As insect ovicides the formula I compounds are particularly effective for reducing the hatch of eggs of Lepidoptera, Coleoptera and Diptera. They are likewise highly effective as plant mite ovicides.

Application of the compounds of the invention for the control of insects and acarina is generally facilitated by employing a composition containing an ovicidally effective amount of the compound(s) in combination with an inert agricultural adjuvant. The compositions may be formulated as emulsifiable concentrates, wettable powders, flowable (thixotropic) concentrates, and the like.

In practice, these compositions are generally dispersed in water or other inexpensive liquid diluent and applied as a spray to the foliage and stems of plants sought to be protected against attack from newly hatching larvae and the adults of the pests.

Desired control is generally achieved with liquid compositions containing from about 1.0 ppm to about 1000 ppm of active ingredient applied at a rate of between about 10 and 50 liters per hectare using aerial application equipment or from about 50 to 1000 liters per hectare using ground application equipment. For mosquito control, the active ingredient may be dispersed in ponds, lakes, rivers or the like in an amount sufficient to provide at least about 0.04 ppm of the active ingredient.

A typical emulsifiable concentrate which may be used in the preparation of the above-identified compositions is as follows:

EMULSIFIABLE CONCENTRATE

50% by weight of cyanomethyl p-methoxybenzyl trithiocarbonate
38% by weight of cyclohexanone
12% by weight of a nonionic emulsifier A typical flowable concentrate may be prepared as follows:

FLOWABLE CONCENTRATE

45% by weight of cyanomethyl p-methoxybenzyl trithiocarbonate
50% by weight of water
3% by weight of sugarfree, sodium based sulfonates of Kraft lignin, and 2% by weight of Bentonite clay.

The ovicidal compositions of this invention are most effective for preventing the hatch of eggs of insects and acarina when brought into direct contact with the eggs; however, we have determined that certain of the formula I cyanomethyl trithiocarbonates, particularly $C_1$-$C_4$ alkyl cyanomethyl trithiocarbonates, advantageously also exhibit fumigant activity and this activity markedly enhances the usefulness of these compounds. Such activity permits control of egg hatch and/or development of newly emerged larvae or nymphs, by application of the active compound to the locus of the deposited eggs such that the toxicant vapors can come in contact with the eggs and/or emerging larvae or nymphs.

Since eggs of Lepidoptera, Coleoptera, Diptera and mites are frequently deposited on the underside of the plant leaves, it is apparent that where dense foliage is encountered, as for example in crops such as soybeans, cotton, tomatoes, potatoes, alfalfa and flowering ornamentals, the fumigant activity of the compound can measureably improve the performance thereof in protecting the treated crops from attack by insects and acarina.

The present invention is further illustrated by the examples set forth below.

EXAMPLE 1

Preparation of Potassium p-Chlorobenzyl Trithiocarbonate

To a flask containing 100 ml of water and 13.0 g (200 mmol) of 86.4% KOH is added 26.4 ml (31.7 g, 200 mmol) of 4-chlorobenzyl mercaptan at 20° C. Then 100 ml of toluene and 100 mg of tetrabutylammonium bisulfate, a phase transfer catalyst, is added and the reaction mixture stirred for 0.5 hours. The reaction mixture is cooled to 18° C. and 26.6 ml (220 mmol) of carbon disulfide is added. After stirring for 0.5 hours, the yellow color of the water layer indicates the formation of the potassium salt of p-chlorobenzyl trithiocarbonic acid.

EXAMPLE 2

Preparation of p-Chlorobenzyl Cyanomethyl Trithiocarbonate

The reaction mixture from Example 1 containing potassium p-chlorobenzyl trithiocarbonate is stirred for 0.5 hours and 12.9 ml (200 mmol) of chloroacetonitrile is then added. The temperature of the reaction mixture is adjusted to 20° to 25° C. and stirring is continued for 2 hours. The yellow color from the aqueous layer transfers to the toluene layer and the toluene layer is then separated therefrom, washed with water, brine and dried with $Na_2SO_4$. The mixture is filtered and concentrated. The residue is taken up in ether-hexane, reduced in volume and crystallized in a freezer. Recrystallization of this material from ether-hexane gives 28.5 g of p-chlorobenzyl cyanomethyl trithiocarbonate, m.p. 41°–43° C.

EXAMPLE 3

Preparation of Potassium Methyl Trithiocarbonate

To a solution of 66 g of 85% KOH (1.0 mol) in 600 ml of absolute ethanol cooled to 0°–10° C. is added 61 ml (1.09 mol) of methyl mercaptan while maintaining the temperature of the reaction mixture at 10° C. The reaction mixture is stirred for 45 minutes and then 66 ml (1.08 mol) of carbon disulfide added thereto while maintaining the temperature of the reaction mixture at 10° C. The mixture is stirred for 15 minutes, then excess ethanol removed under vacuum. The residue is treated with 700 ml of a 1:1 ether-methylene chloride mixture, cooled in an ice bath and filtered. The potassium methyl trithiocarbonate, a yellow solid, is dried and weighs 154.7 g.

Following the above procedure but substituting isopropyl mercaptan or phenethyl mercaptan for methyl mercaptan yields respectively potassium isopropyl trithiocarbonate and potassium phenethyl trithiocarbonate.

EXAMPLE 4

Preparation of Cyanomethyl Methyl Trithiocarbonate

To a solution of 40 mmol of potassium methyl trithiocarbonate from Example 3 in 100 ml of tetrahydrofuran is added 2.6 ml (40 mmol) of chloroacetonitrile while maintaining the temperature of the reaction mixture at from 20°–25° C. The mixture is stirred for 1 hour and then concentrated in vacuo. The oily residue is taken up in ether, washed with water and brine, and distilled to give the cyanomethyl methyl trithiocarbonate, boiling point 115°–116° C. at 0.45 mm Hg.

EXAMPLE 5

Preparation of Cyanomethyl Isopropyl Trithiocarbonate

To a two phase system containing 100 ml of water, 100 ml of toluene, 19.0 g (100 mmol) of potassium isopropyl trithiocarbonate and 50 mg of tetrabutyl ammonium bisulfate, a phase transfer catalyst, is added 6.3 ml (100 mmol) of chloroacetonitrile. The temperature of the reaction is maintained at between 20° and 30° C. After 4.5 hours the layers are separated and the toluene layer washed with water, brine, dried with $Na_2SO_4$, filtered, and concentrated in vacuo. The residue is distilled to give 11.4 g of isopropyl cyanomethyl trithiocarbonate as a yellow oil, boiling point 110°–113° C. at 0.1 mm Hg.

Following the above procedure but substituting potassium t-butyl trithiocarbonate for potassium isopropyl trithiocarbonate yields the product, t-butyl cyanomethyl trithiocarbonate, b.p. 120°–125° C./0.2 mm Hg.

EXAMPLE 6

Preparation of Cyanomethyl Phenethyl Trithiocarbonate

To a solution containing 10.1 g (40 mmol) of potassium phenethyl trithiocarbonate in 100 ml of tetrahydrofuran is added 2.6 ml (40 mmol) of chloroacetonitrile while maintaining the temperature of the reaction mixture at 20°–25° C. The mixture is stirred for 1 hour and concentrated in vacuo. The residue is then taken up in ether, washed with brine, dried with $Na_2SO_4$, filtered and concentrated in vacuo. The residue is crystallized from an ether-hexane mixture to give 9.7 g of a yellow solid, cyanomethyl phenethyl trithiocarbonate, melting point 72°–73° C.

EXAMPLE 7

Preparation of Cyanomethyl α-Methylbenzyl Trithiocarbonate

To a solution of 5.6 g (50 mmol) of potassium t-butoxide in 100 ml of tetrahydrofuran is added 8.7 ml (8.94 g, 60 mmol) of 92% 1-phenylethylmercaptan while maintaining the temperature of the reaction mixture between 20° and 25° C. The resulting suspension is cooled to 18° C. and 4.35 ml (72 mmol) of carbon disulfide is added thereto. The yellow solution which forms is stirred for 0.5 hours and then 3.23 ml (50 mmol) of chloroacetonitrile is added while the temperature of the reaction mixture is maintained at about 20° C. After stirring for 0.5 hour, the mixture is concentrated in vacuo. The residue is taken up in ether and the ether solution washed with water, brine, dried with $Na_2SO_4$ and concentrated in vacuo. The residue is chromatographed on a silica gel dry-column and eluted with 1:2 $CH_2Cl_2$-hexane. The yellow band is collected to give 11.25 g (89%) of a yellow oil, cyanomethyl α-methylbenzyl trithiocarbonate.

Analysis calculated: C, 52.13; H, 4.38; N, 5.53; Found: C, 52.22; H, 4.51; N, 5.33.

Following the above procedure but substituting the appropriate mercaptan for 1-phenylethylmercaptan yields the following products:

Cyanomethyl ethyl trithiocarbonate, bp 115°–117° C./0.2 mm Hg;

Cyanomethyl propyl trithiocarbonate, bp 115°–119° C./0.25 mm Hg;

Cyanomethyl butyl trithiocarbonate, bp 131°–138° C./0.25 mm Hg;

Cyanomethyl sec-butyl trithiocarbonate, bp 112°–118° C./0.1 mm Hg;

Cyanomethyl isobutyl trithiocarbonate, yellow oil

Cyanomethyl pentyl trithiocarbonate, bp 129°–131° C./0.1 mm Hg;

Cyanomethyl tert-pentyl trithiocarbonate, yellow oil;

Cyanomethyl hexyl trithiocarbonate, bp 149°–151° C./0.1 mm Hg;

Cyanomethyl heptyl trithiocarbonate, bp 150° C./0.05 mm Hg;

Cyanomethyl octyl trithiocarbonate, yellow oil;

Benzyl cyanomethyl trithiocarbonate, m.p. 44°–45° C.;

Cyanomethyl 3-phenylpropyl trithiocarbonate, yellow oil;

Cyanomethyl p-methylbenzyl trithiocarbonate, m.p. 62.5°–63° C.;

p-Chlorobenzyl cyanomethyl trithiocarbonate, m.p. 41°–43° C.;

Cyanomethyl o-methylbenzyl trithiocarbonate, m.p. 61.5°–62° C.;
Cyanomethyl 2,4-dichlorobenzyl trithiocarbonate, m.p. 64° C.;
Cyanomethyl 3,4-dichlorobenzyl trithiocarbonate, yellow oil;
Cyanomethyl p-methoxybenzyl trithiocarbonate, m.p. 59°–60° C.;
Cyanomethyl furfuryl trithiocarbonate, m.p. 50°–51.5° C.;
Cyanomethyl cyclohexyl trithiocarbonate, m.p. 53°–54° C.
Cyanomethyl 1-methylcyclohexyl trithiocarbonate, reddish oil;
Cyanomethyl 2,4-dimethylbenzyl trithiocarbonate;
2-Chloro-4-methylbenzyl cyanomethyl trithiocarbonate;
Cyanomethyl 3,4-dimethoxybenzyl trithiocarbonate;
Cyanomethyl 3,5-dimethylbenzyl trithiocarbonate;
2-Chloro-4-methoxybenzyl trithiocarbonate;
Cyanomethyl cyclohexylmethyl trithiocarbonate.

EXAMPLE 8

Evaluation as ovicidal agents of compounds having the structure: R—Z—CS—SCH$_2$CN is determined using the procedures, insects and acarina described below.

Tobacco Budworm (*Heliothis virescens*) egg test

A cotton plant with the first true leaf expanded to about 7 cm in length is dipped in a 50/50 acetone/water mixture containing 100, 10 or 1 ppm of test compound. A 10 to 20 mm square of cheesecloth containing 50–100 budworm eggs 6 to 30 hours old is also dipped in the test solution, placed on the treated leaf and the combination placed in a hood to air dry. When dry, the leaf with egg cloth still attached is removed from the plant and placed in a 250 g cup to which a 5 cm length of damp cotton dental wick has been previously added. A clear plastic lid is placed on the cup and the cup held at 27° C. for 2 days. After 2 days the leaf and cheesecloth are examined under a low power microscope to determine egg hatch. Data obtained are reported below as percent mortality of the eggs (Table I). Malaria mosquito (*Anopheles quadrimaculatus*), eggs and 1st Instar Test Test solutions are prepared as 50/50 acetone/water mixtures containing 0.4 or 0.04 ppm of test compound. A 250 ml test solution is placed in a 400 ml beaker and a wax paper ring about one cm wide and 6.5 cm in diameter is floated on the surface of the test solution to keep the eggs from floating up the meniscus curve and drying out on the side of the beaker and about 100 eggs (6 to 30 hours old) are then introduced into the test solution. After the beaker is held at 27° C. for 2 days, the contents are examined and the percent kill of eggs noted and recorded. Percent kill of newly-hatched larvae and delayed hatch are likewise noted if such occur. Data obtained are reported in (Table I).

Phosphate resistant 2-Spotted Spider Mite (*Tetranychus urticae*) egg, nymph and adult test Sieva lima bean plants with primary leaves 7–8 cm long are cut back to one plant per pot. About 1 to 3 hours before use, the plants are infested with mites to allow them to move over the test plant and deposit their eggs. The infested plants are then dipped for 3 seconds in a 50/50 acetone/water test solution containing 300, 100 or 10 ppm of test compound. The plants are then placed in a hood to dry and then held for 2 days at 27° C. for the first observation. After 2 days, one leaf is removed and examined under a 10X microscope to determine the mortality of the adult mites. The second leaf is examined similarly 7 days after treatment to observe egg kill and mortality of newly hatched nymphs. Data obtained are recorded below (Table I).

Tobacco Budworm (*Heliothis virescens*), closed chamber fumigation test

A 15 mg sample of test compound is dissolved in 10 ml of acetone. One ml of this is then pipetted evenly over the bottom of a 150 mm diameter petri dish which is then set aside to allow the acetone to evaporate. This is the equivalent of 1 kg/ha applied on a broadcast basis to the dish. Lower rates may be prepared by appropriate dilutions of the initial test solution. The petri dish is then placed in a 4-liter battery jar covered with a glass lid. The lid has been previously prepared such that a square of cheesecloth with 50 to 100 budworm eggs has been hung on a clip fastened to the underside of the lid with a piece of tape. The eggs are thus suspended 6 to 8 cm below the lid and centered over the petri dish. The battery jar is then held for 3 days at 27° C. After three days, the eggcloths are examined under a 10X microscope and the eggs counted as dead, hatched or infertile. Percent kill is calculated from: (number dead/number dead+number hatched)×100. Data obtained are reported as percent kill, (Table I).

Cotton Bud Phytotoxicity Test

In this test, 50/50 acetone/water mixtures containing 1000 ppm or 500 ppm of test compound are prepared. Young cotton plants with leaf buds showing are dipped in the test solution and placed in a hood to dry, then held at 27° C. for two weeks to determine whether the cotton buds have been injured by the treatment. Injury is rated on a scale of 0 to 5; 0 being no injury and 5 being complete kill.

Data from the above test are reported in Table I below.

TABLE I

| Structure R—S—CS—SCH$_2$CN | % Kill of Insect Eggs | | | | | | Cotton Bud Phytotoxicity | |
|---|---|---|---|---|---|---|---|---|
| | Mosquito Eggs | | Tobacco Budworm Eggs | | Tobacco Budworm Fumigation Test | | | |
| R | ppm 0.4 | 0.04 | ppm 100 | 10 | 1 kg/ha | 0.1 kg/ha | ppm 1000 | 500 |
| CH$_3$ | 100 | 61–70* | 100 | 71–85* | 100 | 20 | 5 | 5 |
| C$_2$H$_5$ | 100 | 86–99 | 100 | 86–99 | 100 | 80 <10 | 3.5 | 1 |
| n-C$_3$H$_7$ | 100 | 86–99 | 100 | 100 | 100 | 50 <10 | 3 | 2 |
| i-C$_3$H$_7$ | 100 | 0 | 100 | 0 | 100 | 20 <10 | 2.5 | 1 |
| n-C$_4$H$_9$ | 100 | 86–99 | 100 | 86–99 | 59 | 0 | 4 | 1.5 |
| C$_2$H$_5$(CH$_3$)CH— | 100 | 0 | 100 | 0 | 100 | 0 | 5 | 1 |
| (CH$_3$)$_2$CHCH$_2$— | 100 | 0 | 100 | 100 | 100 | 96 | 5 | |
| | | | | | 100 | 96 | 4.5 | 1 |
| (CH$_3$)$_3$C— | 41–60 | 0 | 100 | 100 | 99.5 | 20 <10 | 5 | 5 |
| n-C$_5$H$_{11}$ | 100 | 30–40* | 100 | 100 | <10 | 0 | 5 | 5 |

TABLE I-continued

| | | | | | | | | |
|---|---|---|---|---|---|---|---|---|
| $C_2H_5(CH_3)_2C-$ | 0 | 0 | 100 | 41–60 | 0 | 0 | 5 | 1 |
| n-$C_6H_{13}$ | 100 | 0 | 100 | 100 | <10 | 0 | 5 | 1 |
| n-$C_7H_{13}$ | 100 | 0 | 100 | 71–85 | 0 | 0 | 5 | 5 |
| n-$C_8H_{17}$ | 100 | 0 | 100 | 0 | 0 | 0 | 5 | 5 |
| Benzyl | 100 | 30–40* | 100 | 86–99 | 16 | 0 | 0.5 | 0 |
| Phenylethyl | 100 | 0 | 100 | 100 | 0 | 0 | 2.5 | — |
| 3-Phenylpropyl | 100 | 0 | 0 | — | 0 | — | — | — |
| α-methylbenzyl | 100 | 41–60 | 100 | 0 | 0 | — | 3 | — |
| p-chlorobenzyl | 100 | 86–99 | 100 | 0 | 0 | — | 0 | — |
| p-methylbenzyl | 100 | 41–60 | 100 | 100 | 0 | — | 4 | — |
| o-methylbenzyl | 100 | 41–60 | 100 | 0 | 0 | — | 2 | — |
| 2,4-Dichlorobenzyl | 100 | 0 | 100 | 0 | 50 | — | 5 | — |
| 3,4-Dichlorobenzyl | 100 | 0 | 100 | 0 | 0 | — | 5 | — |
| p-methoxybenzyl | 100 | 0 | 100 | 0 | 16* | — | 0 | — |
| furfyryl | 100 | 0 | 100 | 100 | 0 | — | 3 | — |
| cyclohexyl | 86–99 | 0 | 100 | 100 | <10 | — | 1.5 | — |
| 1-Methylcyclohexyl | 41–60 | 0 | 100 | 41–60 | — | — | 2 | — |

| | % Kill of Insect Eggs | | | | | | | |
|---|---|---|---|---|---|---|---|---|
| Structure R—O—CS—SCH$_2$CN | Mosquito Eggs | | Tobacco Budworm Eggs | | Tobacco Budworm Fumigation Test | | Cotton Bud Phytotoxicity | |
| R | ppm 0.4 | 0.04 | ppm 100 | 10 | 1 kg/ha | 0.1 kg/ha | ppm 1000 | 500 |
| $CH_3$ | 100 | 41–60 | 100 | 61–70 | decompose | — | decompose | |
| $C_2H_5$ | 100 | 0 | 100 | 0 / 100 | 100 | 0 | 3 | 0 |
|  | 100 | 0 | 100 | 41–60 | 9 | — | 5 | |
|  | 100 | 0 | 100 | 100 | 0 | — | 5 | |
| cyclohexyl | 41–60 | 0 | 100 | 41–60 | 0+ | 0+50 | 4 | |

* = Average of two or more tests.

EXAMPLE 9

Assessment of Phytotoxicity of test compounds applied as Foliar Sprays to growing plants The toxicity to growing plants of the compounds of the present invention is evaluated in tests wherein a variety of monocotyledonous and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN ® 20, a polyoxyethylene sorbitan monolaurate surfactant of Atlas Chemical Industries, in sufficient quantity to provide the equivalent of about 10 kg per hectare of active compound when applied to the plants through a spray nozzle operating at 2.81 kg/cm$^2$ pressure for a predetermined time. After spraying, the plants are placed on greenhouse benches and are cared for in the usual manner, commensurate with conventional greenhouse practices. Two weeks after treatment, the seedling plants are examined and rated according to the rating system set forth below. The data obtained are reported in Table II below. From these data it can be seen that the isopropyl, benzyl, p-chlorobenzyl and p-methoxybenzyl cyanomethyl trithiocarbonates are markedly less phytotoxic than cyanomethyl methyl trithiocarbonate.

| Rating System: | % Difference in Growth from the Check* |
|---|---|
| 0-No effect | 0 |
| 1-Possible effect | 1–10 |
| 2-Slight effect | 11–25 |
| 3-Moderate effect | 26–40 |
| 5-Definite injury | 41–60 |
| 6-Herbicidal effect | 61–75 |
| 7-Good herbicidal effect | 76–90 |
| 8-Approaching complete kill | 91–99 |
| 9-Complete kill | 100 |
| 4-Abnormal growth; that is, a definite physiological malformation but with an over-all effect less than a 5 on the rating scale. | |

Plant Abbreviations

PN—Purple nutsedge (*Cyperus rotundus*, L.)
SE—Sesbania (*Sesbania exaltata*)
MU—Mustard (*Brassica kaber*)
PI—Pigweed (*Amaranthus retroflexus*)
RW—Ragweed (*Ambrosia artemisiifolia*)
MG—Morningglory (*Ipomoea purpurea*)
PS—Priky sida (*Sida spinosa L.*)
VL—Velvetleaf (*Abutilon theophrasti*)
BA—Barnyardgrass (*Echinochloa crusgalli*)
CR—Crabgrass (*Digitaria sanguinalis*)
FO—Green Foxtail (*Setaria viridis*)
WO—Wild Oats (*Avena fatua*)

TABLE II

Postemergence Herbicidal Evaluation of test compounds.

| Structure R—S—CS—SCH$_2$—CN R | Rate kg/ha | Plant Species | | | | | | | | | | | |
|---|---|---|---|---|---|---|---|---|---|---|---|---|---|
| | | PN | SE | MU | PI | RW | MG | PS | VI | BA | CR | FO | WO |
| $CH_3$ | 10 | 0 | 9 | 2 | 9 | 7 | 2 | 9 | 9 | 2 | 3 | 9 | 0 |
| $(CH_3)_2CH$ | 10 | 0 | 0 | 0 | 0 | 0 | 0 | 0 | 0 | 0 | 3 | 5 | 0 |
| benzyl | 10 | 0 | 0 | 0 | 0 | 0 | 0 | 0 | 0 | 0 | 0 | 3 | 0 |
| p-chlorobenzyl | 10 | 0 | 0 | 0 | 0 | 0 | 0 | 0 | 0 | 0 | 0 | 0 | 0 |

TABLE II-continued

Postemergence Herbicidal Evaluation of test compounds.

| Structure R—S—CS—SCH₂—CN | Rate | Plant Species | | | | | | | | | | | |
|---|---|---|---|---|---|---|---|---|---|---|---|---|---|
| R | kg/ha | PN | SE | MU | PI | RW | MG | PS | VI | BA | CR | FO | WO |
| p-methoxybenzyl | 10 | 0 | 0 | 0 | 0 | 1 | 0 | 0 | 0 | 6 | 7 | 2 | 0 |

We claim:

1. A cyanomethyl trithiocarbonate compound having the formula:

R—S—CS—SCH₂CN wherein R is α-methylbenzyl,

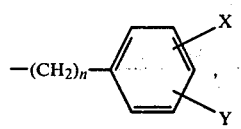

cycloalkyl $C_3$-$C_6$ optionally substituted with methyl, furfuryl or cycloalkyl $C_3$-$C_6$ methyl; X and Y each represent H, Cl, CH₃ or OCH₃ and n is an integer 1, 2 and 3.

2. A compound according to claim 1 wherein R is α-methylbenzyl, furfuryl, cyclohexyl or

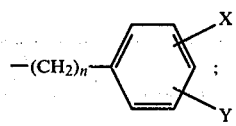

X is H, Cl, CH₃ or OCH₃ and Y is H or Cl provided that when Y is Cl, X is H or Cl.

3. A compound according to claim 1, benzyl cyanomethyl trithiocarbonate.

4. A compound according to claim 1, cyanomethyl p-methoxybenzyl trithiocarbonate.

5. A compound according to claim 1, cyanomethyl furfuryl trithiocarbonate.

6. A compound according to claim 1, cyanomethyl cyclohexyl trithiocarbonate.

7. A compound according to claim 1, cyanomethyl o-methylbenzyl trithiocarbonate.

8. A compound according to claim 1, cyanomethyl p-methylbenzyl trithiocarbonate.

9. A method for controlling insects and acarina comprising contacting the ova of the insects and acarina with an ovicidally effective amount of a compound of the formula:

R—Z—CS—SCH₂CN wherein Z is O or S, R is $C_1$-$C_8$ alkyl, α-methylbenzyl,

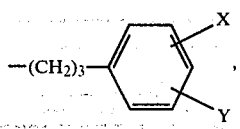

cycloalkyl $C_3$-$C_6$ optionally substituted with methyl, furfuryl, cycloalkyl $C_3$-$C_6$ methyl; X and Y each represent H, Cl, CH₃ or OCH₃ and n is an integer selected from 1, 2 and 3.

10. A method according to claim 9 for controlling insects comprising contacting the ova of the insects with an ovicidally effective amount of a compound according to claim 9 wherein Z is S, R is alkyl $C_1$-$C_8$, α-methylbenzyl, furfuryl, cyclohexyl or

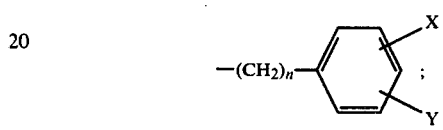

X is H, Cl, CH₃ or OCH₃ and Y is H or Cl, provided that when Y is Cl, X is H or Cl.

11. A method according to claim 9 for controlling plant mites comprising contacting the ova of the plant mites with an ovicidally effective amount of a compound according to claim 9 wherein Z is S, R is sec-butyl, isobutyl, alkyl C $C_5$-$C_8$, α-methylbenzyl, furfuryl, cyclohexyl, methylcyclohexyl or

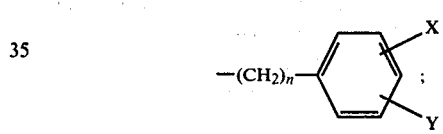

X is H, Cl, CH₃ or OCH₃ and Y is H or Cl, provided that when Y is Cl, X is H or Cl.

12. A method according to claim 9, wherein the cyanomethyl trithiocarbonate is applied to the locus wherein the insect and acarina eggs are deposited, in the form of a liquid spray containing from about 1.0 ppm to about 1000 ppm of the trithiocarbonate compound and at a rate of from 10 to 1000 liters of said liquid per hectare.

13. A method according to claim 9, wherein the compound is cyanomethyl $C_2$-$C_4$ alkyl trithiocarbonate.

14. A method according to claim 9, wherein the compound is benzyl cyanomethyl trithiocarbonate.

15. A method according to claim 9, wherein the compound is cyanomethyl p-methoxybenzyl trithiocarbonate.

16. A method according to claim 9, wherein the compound is cyanomethyl furfuryl trithiocarbonate.

17. A method according to claim 13, wherein the compound is cyanomethyl methyl trithiocarbonate.

18. A method according to claim 9, wherein the compound is cyanomethyl cyclohexyl trithiocarbonate.

19. A method according to claim 9, wherein the compound is cyanomethyl o-methylbenzyl trithiocarbonate.

20. A method according to claim 9, wherein the compound is cyanomethyl p-methylbenzyl trithiocarbonate.

* * * * *